US012752007B2

(12) United States Patent
Xu et al.

(10) Patent No.: US 12,752,007 B2
(45) Date of Patent: Oct. 6, 2026

(54) INDUCIBLE CHIMERIC ANTIGEN RECEPTOR AND APPLICATION THEREOF

(71) Applicant: Beijing Tiantan Hospital, Capital Medical University, Beijing (CN)

(72) Inventors: Jun Xu, Beijing (CN); Yanli Wang, Beijing (CN); Jiwei Jiang, Beijing (CN); Zhongli Du, Beijing (CN); Zhenlan Du, Beijing (CN)

(73) Assignee: Beijing Tiantan Hospital, Capital Medical University, Beijing (CN)

( * ) Notice: Subject to any disclaimer, the term of this patent is extended or adjusted under 35 U.S.C. 154(b) by 770 days.

(21) Appl. No.: 18/179,335

(22) Filed: Mar. 6, 2023

(65) Prior Publication Data

US 2024/0058445 A1 Feb. 22, 2024

(30) Foreign Application Priority Data

Apr. 24, 2022 (CN) ......................... 202210433024.0

(51) Int. Cl.

| | |
|---|---|
| ***A61K 40/31*** | (2025.01) |
| ***A61K 35/17*** | (2015.01) |
| ***A61P 25/28*** | (2006.01) |
| ***C07K 16/28*** | (2006.01) |
| ***C12N 5/0783*** | (2010.01) |

(52) U.S. Cl.

CPC .............. *A61K 40/31* (2025.01); *A61K 35/17* (2013.01); *A61P 25/28* (2018.01); *C07K 16/2866* (2013.01); *C12N 5/0636* (2013.01); *A61K 2239/13* (2023.05); *A61K 2239/22* (2023.05); *C07K 2317/53* (2013.01); *C07K 2317/622* (2013.01); *C12N 2510/00* (2013.01)

(58) Field of Classification Search

CPC .... A61K 40/31; A61K 35/17; A61K 2239/13; A61K 2239/22; A61K 40/11; A61K 40/4216; A61K 39/0007; A61K 2039/5158; A61P 25/28; C07K 16/2866; C07K 2317/53; C07K 2317/622; C07K 2319/03; C07K 14/7051; C07K 2319/00; C12N 5/0636; C12N 2510/00; C12N 15/86; C12N 2740/15043

See application file for complete search history.

(56) References Cited

U.S. PATENT DOCUMENTS

2019/0292240 A1* 9/2019 Pulé .................. A61K 40/4211

FOREIGN PATENT DOCUMENTS

| | | | | |
|---|---|---|---|---|
| CN | 108276495 A | * | 7/2018 | ......... C07K 16/2866 |
| WO | WO-2015058018 A1 | * | 4/2015 | ....... C07K 14/70517 |
| WO | WO-2016189045 A1 | * | 12/2016 | ............. A61P 25/18 |
| WO | WO-2020232165 A1 | * | 11/2020 | ......... C07K 16/2809 |

OTHER PUBLICATIONS

Giuntini et al. Clin Vaccine Immunol. Aug. 5, 2016;23(8):698-706. (Year: 2016).*

Han et al. Cell Mol Life Sci Apr. 2, 2022;79(4):219 (Year: 2022).*

* cited by examiner

*Primary Examiner* — Sean E Aeder
*Assistant Examiner* — Yie Chia Lee

(57) ABSTRACT

An inducible chimeric antigen receptor and its application relate to the field of immune therapy. The inducible antigen receptor includes a single-chain variable fragment (scFv) antibody against human CSF1R, a truncated hIgG1 hinge region SH, a T cell co-stimulatory signaling molecule, and a T cell cytoplasmic signaling domain. Transcription of the chimeric antigen receptor is regulated by an inducible expression element tet operator. The induce chimeric antigen receptor molecules can be used to modify T lymphocytes, eliminating the cytokine storm problem of CAR-T cells in the treatment of Alzheimer's disease (AD), and achieving target treatment of AD.

10 Claims, 8 Drawing Sheets

Specification includes a Sequence Listing.

SEQUENCE LISTING

```
Sequence total quantity: 9
SEQ ID NO: 1            moltype = DNA  length = 1497
FEATURE                 Location/Qualifiers
source                  1..1497
                        mol_type = other DNA
                        organism = synthetic construct
SEQUENCE: 1
atggccctgc ccgtgaccgc tctgctgctg cctctggccc tgctgctgca cgccgctaga  60
cccgaggtgc agctggtgga atccggcggc ggcctggtgc agcctggagg atctctgaaa  120
ctgagttgcg ccgcctccgg cttcaccttc tctgacgcct ggatggactg ggtgagacag  180
agtcccgaaa tggggctgga gtgggttgct gagattagat ccaaggcaaa taaccacgcc  240
acattctacg ccgagtctgt taaaggcagg tttaccatta gcagagacga cagcaaatcc  300
tccgtgtacc tgcaaatgaa cagcctcaga gccgaggaca caggcatcta ctactgcacc  360
agagtgaagg tgggcttcga caattgggga cagggaacca ccctgacagt gagctccggc  420
ggcggaggca gcggaggagg aggatcagga ggaggaggca gtgacatcca gatgacacag  480
agccccagtt cactgagcgc cagcgtgggc gatagagtga ccatcacctg cagggctagt  540
gagaatatct atagtaacct ggcttggtac cagcagaagg acggcaaaag cccccaactg  600
ctcgtgcacg ccgccaccaa cctggccgac ggagtgccta gcagattcag cggaagcggc  660
agcgggaccc agtactccct gactatcagc agcctccagc ccgaagactt cggctcctac  720
tattgccagc acttctgggg tacccccaga acctttggcg gcggcaccaa gctggagatc  780
aaggagccca aatcttgtga caaaactcac acatgcccac cgtgcccgtt ttgggtgctg  840
gtggtggttg gtggagtcct ggcttgctat agcttgctag taacagtggc ctttattatt  900
ttctgggtga ggagtaagag gagcaggctc ctgcacagtg actacatgaa catgactccc  960
cgccgccccg ggcccacccg caagcattac cagccctatg ccccaccacg cgacttcgca  1020
gcctatcgct ccaaacgggg cagaaagaaa ctcctgtata tattcaaaca accatttatg  1080
agaccagtac aaactactca agaggaagat ggctgtagct gccgatttcc agaagaagaa  1140
```

-continued

```
gaaggaggat gtgaactgag agtgaagttc agcaggagcg cagacgcccc cgcgtaccag  1200
cagggccaga accagctcta taacgagctc aatctaggac gaagagagga gtacgatgtt  1260
ttggacaaga gacgtggccg ggaccctgag atggggggaa agccgagaag gaagaaccct  1320
caggaaggcc tgtacaatga actgcagaaa gataagatgg cggaggccta cagtgagatt  1380
gggatgaaag gcgagcgccg gaggggcaag gggcacgatg gcctttacca gggtctcagt  1440
acagccacca aggacaccta cgacgccctt cacatgcagg ccctgccccc tcgctaa     1497

SEQ ID NO: 2            moltype = AA  length = 498
FEATURE                 Location/Qualifiers
source                  1..498
                        mol_type = protein
                        organism = synthetic construct
SEQUENCE: 2
MALPVTALLL PLALLLHAAR PEVQLVESGG GLVQPGGSLK LSCAASGFTF SDAWMDWVRQ  60
SPEMGLEWVA EIRSKANNHA TFYAESVKGR FTISRDDSKS SVYLQMNSLR AEDTGIYYCT  120
RVKVGFDNWG QGTTLTVSSG GGGSGGGGSG GGGSDIQMTQ SPSSLSASVG DRVTITCRAS  180
ENIYSNLAWY QQKDGKSPQL LVHAATNLAD GVPSRFSGSG SGTQYSLTIS SLQPEDFGSY  240
YCQHFWGTPR TFGGGTKLEI KEPKSCDKTH TCPPCPFWVL VVVGGVLACY SLLVTVAFII  300
FWVRSKRSRL LHSDYMNMTP RRPGPTRKHY QPYAPPRDFA AYRSKRGRKK LLYIFKQPFM  360
RPVQTTQEED GCSCRFPEEE EGGCELRVKF SRSADAPAYQ QGQNQLYNEL NLGRREEYDV  420
LDKRRGRDPE MGGKPRRKNP QEGLYNELQK DKMAEAYSEI GMKGERRRGK GHDGLYQGLS  480
TATKDTYDAL HMQALPPR                                              498

SEQ ID NO: 3            moltype = AA  length = 21
FEATURE                 Location/Qualifiers
source                  1..21
                        mol_type = protein
                        organism = synthetic construct
SEQUENCE: 3
MALPVTALLL PLALLLHAAR P                                          21

SEQ ID NO: 4            moltype = AA  length = 13
FEATURE                 Location/Qualifiers
source                  1..13
                        mol_type = protein
                        organism = synthetic construct
SEQUENCE: 4
PKSCDKTHTC PPC                                                   13

SEQ ID NO: 5            moltype = DNA  length = 368
FEATURE                 Location/Qualifiers
source                  1..368
                        mol_type = other DNA
                        organism = synthetic construct
SEQUENCE: 5
tttacgaggg taggaagtgg tacggaaagt tggtataaga caaaagtgtt gtggaattga  60
agtttactca aaaaatcagc actcttttat aggcgccctg gtttacataa gcaaagctta  120
tacgttctct atcactgata gggagtaaac tggatatacg ttctctatca ctgataggga  180
gtaaactgta gatacgttct ctatcactga tagggagtaa actggtcata cgttctctat  240
cactgatagg gagtaaactc cttatacgtt ctctatcact gatagggagt aaagtctgca  300
tacgttctct atcactgata gggagtaaac tcttcatacg ttctctatca ctgataggga  360
gtaaactc                                                         368

SEQ ID NO: 6            moltype = AA  length = 15
FEATURE                 Location/Qualifiers
source                  1..15
                        mol_type = protein
                        organism = synthetic construct
SEQUENCE: 6
GGGGSGGGGS GGGGS                                                 15

SEQ ID NO: 7            moltype = AA  length = 240
FEATURE                 Location/Qualifiers
source                  1..240
                        mol_type = protein
                        organism = synthetic construct
SEQUENCE: 7
EVQLVESGGG LVQPGGSLKL SCAASGFTFS DAWMDWVRQS PEMGLEWVAE IRSKANNHAT  60
FYAESVKGRF TISRDDSKSS VYLQMNSLRA EDTGIYYCTR VKVGFDNWGQ GTTLTVSSGG  120
GGSGGGGSGG GGSDIQMTQS PSSLSASVGD RVTITCRASE NIYSNLAWYQ QKDGKSPQLL  180
VHAATNLADG VPSRFSGSGS GTQYSLTISS LQPEDFGSYY CQHFWGTPRT FGGGTKLEIK  240

SEQ ID NO: 8            moltype = DNA  length = 44
FEATURE                 Location/Qualifiers
source                  1..44
                        mol_type = other DNA
                        organism = synthetic construct
SEQUENCE: 8
gaggtggtct ggatccttag cgagggggca gggcctgcat gtga                 44
```

-continued

```
SEQ ID NO: 9            moltype = DNA  length = 42
FEATURE                 Location/Qualifiers
source                  1..42
                        mol_type = other DNA
                        organism = synthetic construct
SEQUENCE: 9
ccctcgtaaa gaattcatgg ccctgcccgt gaccgctctg ct                    42
```

INDUCIBLE CHIMERIC ANTIGEN RECEPTOR AND APPLICATION THEREOF

CROSS REFERENCE OF RELATED APPLICATIONS

This application claims priority of Chinse Patent Application No. 202210433024.0, filed on Apr. 24, 2022, entitled "Inducible Chimeric Antigen Receptor and Application thereof," in the China National Intellectual Property Administration (CNIPA), the entire contents of which are hereby incorporated by reference in their entireties.

REFERENCE TO AN ELECTRONIC SEQUENCE LISTING

The contents of the electronic sequence listing (CAR-XML.xml; Size: 13,109 bytes; and Date of Creation: Aug. 4, 2023) is herein incorporated by reference in its entirety.

FIELD OF THE DISCLOSURE

The disclosure relates to the technical field of immunotherapy, more particularly to an inducible chimeric antigen receptor and an application thereof.

BACKGROUND OF THE DISCLOSURE

The global phenomenon of aging populations has resulted in the prevalence of age-related dementia such as Alzheimer's disease (AD) surpassing 50 million cases in 2016, leading to a significant financial burden from direct medical costs and indirect caregiving expenses. Despite the availability of drugs to mitigate symptoms, AD has yet to find a cure or effective means of slowing its progression, with over 3,000 drug candidates having failed in the past 16 years. Targeted therapies solely focusing on the pathological features of AD, such as β-amyloid and phosphorylated tau, have proven challenging to succeed with a "band-aid" approach. A novel strategy for therapeutic intervention would require a multi-targeted approach, exploring pathological mechanisms that promote disease progression, such as chronic inflammation. The US FDA has declared a significant shift in the development of new drugs for AD, endorsing early intervention (Phase 1 and 2) rather than the previous focus on more advanced stages (Phases 3 and 4) where there is clear cognitive impairment. The new approach emphasizes the use of biomarkers as clinical endpoints and targets the disease during its early stages when pathology is present but clinical symptoms are not yet apparent (Phase 1) or when minimal and measurable neurological abnormalities are present on the basis of pathological changes (Phase 2) without functional decline.

Chimeric antigen receptor-modified T cells (CAR-T) are composed of an antigen-specific receptor that recognizes and binds monoclonal antibodies, consisting of a single-chain variable fragment (scFv), extracellular spacer sequences, transmembrane domains, and intracellular T cell activation domains. As one of the specific cell-based immunotherapies, CAR-T cells have been making remarkable progress in the field of cancer treatment. As one of the specific cell-based immunotherapies, CAR-T cells have been making remarkable progress in the field of cancer treatment. M1 type microglial cells are the primary cells responsible for inducing neuroinflammation and play a clear promoting role in the occurrence and development of AD. CSF1R, which is highly expressed on the surface of M1 type microglia cells, is an ideal therapeutic target for targeted therapy. Thus, CAR-T cell therapy targeting CSF1R holds theoretical promise in the treatment of AD. However, due to the strong targeted killing effect of CAR-T cells, they can rapidly kill a large number of target cells in a short period of time, leading to the release of a large amount of cytokines and triggering a "cytokine storm" (CRS). Therefore, controlling the side effects of CRS is especially important in clinical treatment.

SUMMARY OF THE DISCLOSURE

In consideration of these concerns, the object of this disclosure is to provide a chimeric antigen receptor (CAR) with an inducible expression system, enabling controlled modulation of the CAR gene expression level. This approach mitigates the potential adverse effect of cytokine storms that may arise upon CAR-T cell therapy intervention.

In order to address the technical problems above, the present disclosure provides the following solutions.

The disclosure provides a chimeric antigen receptor, which includes a single-chain variable fragment (scFv) antibody against human CSF1R, a truncated hIgG1 hinge region SH, a T cell co-stimulatory signaling molecule, and a T cell intracellular signaling domain. The transcription of the chimeric antigen receptor is regulated by an inducible expression element, which is a tet operator.

In some embodiments, the nucleotide sequence of the tet operator is shown as SEQ ID NO. 5.

In some embodiments, the amino acid sequence of the truncated hIgG1 hinge region SH is shown as SEQ ID NO. 4.

In some embodiments, the T cell co-stimulatory signaling molecule includes one or more of CD28, 41BB, and OX40.

In some embodiments, the intracellular signaling domain of the T cell comprises the CD3 zeta intracellular signaling activation domain.

In some embodiments, the N-terminus of the chimeric antigen receptor is connected to a signal peptide with an amino acid sequence as shown in SEQ ID NO. 3.

In some embodiments, the nucleotide sequence of the chimeric antigen receptor is shown as SEQ ID NO. 1, and the amino acid sequence of said chimeric antigen receptor is shown as SEQ ID NO. 2.

The disclosure provides a recombinant lentivirus. The recombinant lentivirus includes the above-mentioned chimeric antigen receptor.

The disclosure further provides a CAR-T cell expressing the aforementioned chimeric antigen receptor, or including the aforementioned recombinant lentivirus carrying the chimeric antigen receptor.

The disclosure also provides the use of the aforementioned chimeric antigen receptor, recombinant lentivirus, or CAR-T cells in the preparation of drugs for the treatment of Alzheimer's disease.

The present disclosure provides a chimeric antigen receptor (CAR) that can be prepared using a viral vector to obtain lentiviral pseudovirus particles containing the CAR. The lentiviral pseudovirus particles can be used to transduce and activate T cells, resulting in the production of inducible CAR-T cells. The expression time and level of the CAR in the present disclosure are regulated by the induction agent DOX in terms of time and dose. In the presence of DOX, CAR-T cells specifically kill CSF1R-positive target cells and secrete cytokines including IL-2 and IFN-γ. In the absence of DOX, CAR-T cells rarely kill CSF1R-positive cells, and no longer secrete IL-2 and IFN-γ. Experimental results have demonstrated that the CAR-T cells of the present disclosure can regulate the killing of target cells, thereby improving the targeting of AD treatment. Furthermore, the present disclosure achieves control of CAR gene expression levels through an inducible expression system, which can regulate cytokine secretion levels and effectively avoid the potential side effect of a "cytokine storm" that may be triggered by CAR-T cell therapy.

DETAILED DESCRIPTION OF THE DISCLOSURE

Figure 1:
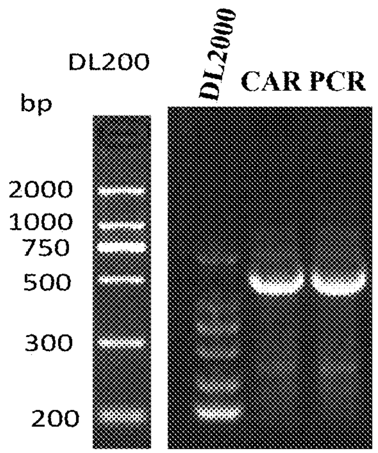
FIG. 1 shows the DNA fragment of the synthesized CSF1R CAR gene amplified by PCR according to the present disclosure.

The present disclosure provides a chimeric antigen receptor including a single-chain variable fragment (scFv) antibody against human CSF1R, a truncated hIgG1 hinge region SH, a T cell co-stimulatory signaling molecule, and a T cell intracellular signaling domain. The transcription of the chimeric antigen receptor is regulated by an inducible expression element, which is a tet operator.

In the present disclosure, the tet operator includes a tTA-binding element, and the nucleotide sequence of the tet operator is preferably as shown in SEQ ID NO. 5. The tet operator in the present disclosure can induce and regulate the expression of the CAR. The scFv in the present disclosure is preferably derived from a monoclonal antibody against human CSF1R protein produced by a mouse. The amino acid sequence of the scFv is as shown in SEQ ID NO. 7. The truncated hIgG1 hinge region SH in the present disclosure is preferably composed of the amino acid sequence: Pro Lys Ser Cys Asp Lys Thr His Thr Cys Pro Pro Cys (SEQ ID NO. 4). The truncated hIgG1 hinge region can reduce the distance between CAR-T cells and tumor cells, thereby endowing the CAR-T cells with stronger tumor-killing ability.

In the present disclosure, preferably, the T cell co-stimulatory signaling molecules include one or more of CD28, 41BB, and OX40. Preferably, the T cell intracellular signaling domain is the CD3 Zeta intracellular signaling activation domain. In this disclosure, preferably, the concatenation of the T cell co-stimulatory signaling molecules and the T cell intracellular signaling domain is used as an intracellular activation domain. Preferably, intracellular activation domain includes CD28-OX40-CD3zeta, CD28-CD3zeta, 41BB-CD3zeta, and CD28-41BB-CD3zeta.

Preferably, the amino-terminal signal peptide of the chimeric antigen receptor in the present disclosure is shown in SEQ ID NO. 3. Preferably, the signal peptide is selected to be cleaved off after CAR expression and can guide the protein to locate on the cell membrane.

Preferably, the nucleotide sequence of the chimeric antigen receptor provided by the present disclosure is shown as SEQ ID NO. 1, and the amino acid sequence of the chimeric antigen receptor is shown as SEQ ID NO. 2. Preferably, the consenting peptide sequence between the heavy and light chain molecules of the CAR is (gly4ser)3, specifically Gly Gly Gly Gly Ser Gly Gly Gly Gly Ser Gly Gly Gly Gly Ser (SEQ ID NO. 6).

In this disclosure, a recombinant lentivirus containing the aforementioned chimeric antigen receptor is provided. The scFv sequence is humanized and optimized with a signal peptide sequence added at the 5' end and SH-intracellular activation domain added at the 3' end. The entire gene is synthesized and cloned into an inducible lentiviral backbone vector to obtain the recombinant lentivirus. There are no specific limitations on the lentiviral backbone vector used in this disclosure, and conventional lentiviral backbone vectors in the art may be used.

The present disclosure provides a CAR-T cell, which expresses the aforementioned chimeric antigen receptor, or includes the aforementioned recombinant lentivirus. Preferably, the CAR-T cells of the present disclosure are obtained by transducing and activating T cells after the aforementioned recombinant lentivirus and auxiliary plasmids co-transduction into 293T cells to generate self-inactivating lentiviral pseudoparticles. The auxiliary plasmids of the present disclosure, preferably, include PMD2G and pSPAX2. The CAR-T cells of the present disclosure can be induced to express by an induction agent. Preferably, the induction agent is doxycycline (DOX). In the presence of DOX, CAR-T cells selectively kill CSF1R-positive target cells, and secrete cytokines IL-2 and IFN-γ. After the induction agent DOX is withdrawn, CAR-T cells rarely kill CSF1R-positive cells, and no longer secrete cytokines IL-2 and IFN-γ.

The present disclosure also provides the use of the aforementioned chimeric antigen receptor (CAR), recombinant lentivirus, or CAR-T cells in the preparation of therapeutic drugs for Alzheimer's disease. The disclosure respectively detects the CAR expression with or without the presence of the induction agent, and assesses its cytotoxic effect and cytokine secretion level on CSF1R-positive cells. Thus, the CAR-T cells can eliminate M1-type microglia cells that are CSF1R-positive and can be used as drugs for targeted treatment of AD.

In order to provide a clearer understanding of the objects, technical solutions, and advantages of the present disclosure, detailed explanation are provided below in conjunction with exemplary embodiments. However, it should not be constructed as limiting the scope of the present disclosure.

In the following embodiments, unless otherwise specified, conventional methods are used.

Materials, reagents, culture vessels, etc. used in the following embodiments can be obtained from commercial sources unless otherwise specified.

Embodiment One: Construction of Inducible CSF1R.CAR Lentiviral Vector Clones

1. Amplification of CSF1R CAR DNA Fragment by PCR

As shown in sequence 1, the spliced DNA sequence was synthesized by Nanjing GenScript Biotech Co., Ltd., and the synthesized CSF1R CAR clone was inserted into the pUC57 vector, named pUC57-CSF1RCAR. Using this plasmid as a template, the CSF1RCAR DNA fragment was amplified with specific primers. The sequences of the upstream and downstream primers are as follows:

```
Upstream primer:
                                        (SEQ ID NO. 8)
5'-GAGGTGGTCTGGATCCTTAGCGAGGGGGCAGG

GCCTGCATGTGA-3';

Downstream primer:
                                        (SEQ ID NO. 8)
5'-CCCTCGTAAAGAATTCATGGCCCTGCCCGTG

ACCGCTCTGCT-3'.
```

The amplification reaction system was as follows: 25 μL 2×PrimerSTAR buffer (purchased from Takara), 3 μL of each upstream and downstream primers, 5 ng of pUC57-CSF1RCAR plasmid DNA as the template, and deionized sterile water (DDW) to a final volume of 50 μL.

The PCR amplification conditions were as follows: 98° C. for 10 seconds, 60° C. for 10 seconds, 72° C. for 10 seconds, for a total of 30 cycles, and a final extension at 72° C. for 5 minutes.

The PCR amplification product was separated using agarose gel electrophoresis, as shown in FIG. 1. Based on the agarose gel electrophoresis results, the size of the PCR product was approximately 1500 base pairs (bp), which is consistent with the expected size.

2. Linearization of the Vector.

Preparation of plvx-TetOne-SV40P-Puro plasmid DNA involved double digestion using restriction endonucleases EcoRI and BamHI (NEB company). The reaction system included 2 μg of plasmid DNA, 2 μL of 10×CutSmart buffer, 1 μL of EcoRI and 1 μL of BamHI. The reaction mixture was brought to a final volume of 20 μL using distilled and deionized water (DDW). The digestion reaction was carried out by incubating the mixture at 37° C. in a water bath for 4 hours.

Figure 2:
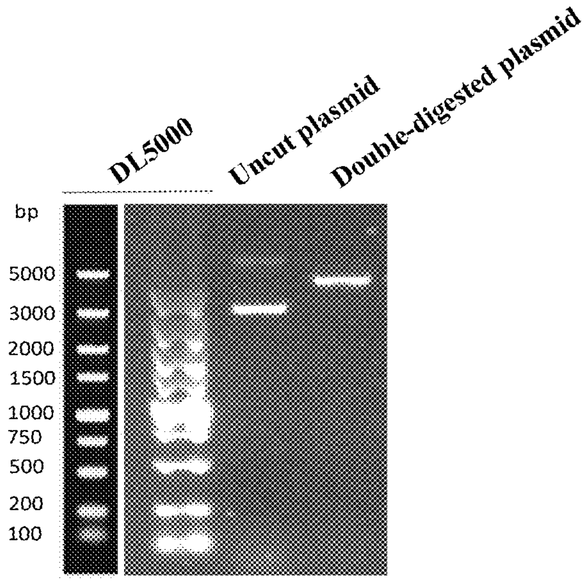
FIG. 2 shows the double enzyme digestion of the vector plasmid DNA according to the present disclosure.

After enzymatic digestion, the products were separated by agarose gel electrophoresis, and the vector DNA was recovered using the agarose gel DNA recovery kit (purchased from Generay Biotechnology Co., Ltd.), as shown in FIG. 2. Based on the results of the agarose gel electrophoresis, the vector DNA was completely linearized.

3. Ligation and Transformation of Insert Fragment and Vector Molecules

The PCR product separated by agarose gel electrophoresis and the vector fragment were mixed at a molar ratio of 4:1. Then, 2 μL of 5× seamless cloning ligation mixture (purchased from Zhenjiang ABM Biotechnology Co., Ltd.) was added, followed by addition of DDW to bring the total volume to 10 μL. The ligation mixture was placed on ice for 30 minutes, then transformed into Stble3 competent bacteria (purchased from Vigen Biotechnology (Zhenjiang) Co., Ltd). After transformation, the bacteria were coated on LB agar petri-dishes containing ampicillin and incubated at 37° C. overnight.

4. Identification and Screening of Positive Recombinant Clones

Ten overnight cultured single colonies were individually picked and mixed thoroughly with 20 μL of DDW. The mixture was boiled for 5 minutes and centrifuged at 13,000 rpm for 5 minutes. Then 2 μL of the supernatant were collected as a template for PCR amplification to screen for positive clones. The PCR amplification reaction system and conditions were the same as those described in step 1.

Figure 3:
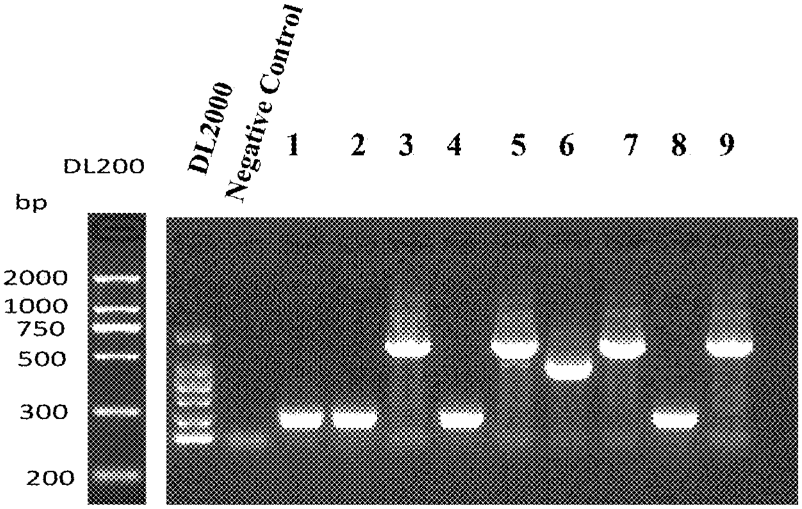
FIG. 3 shows the colony PCR validation result of subcloning the synthetic CAR gene into the inducible lentiviral vector pLVX-TetOn according to the present discourse.
Figure 4:
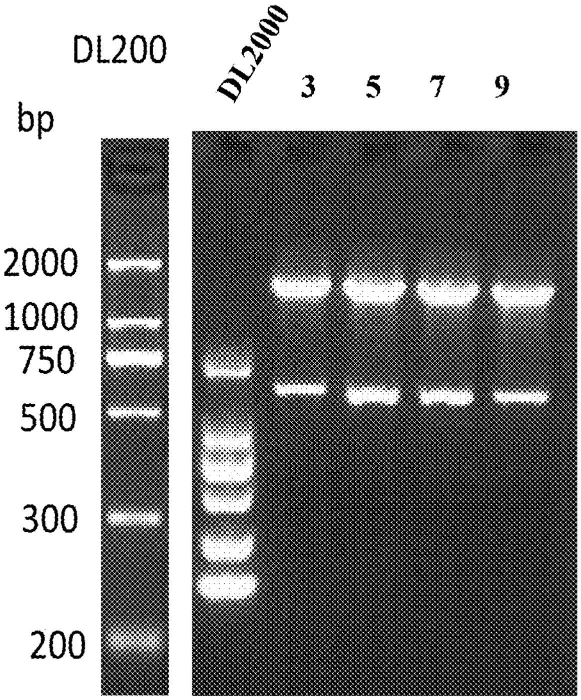
FIG. 4 illustrates the verification of the enzymatic cleavage of the synthesized CAR gene subcloned onto the inducible lentivirus vector pLVX-TetOn according to the present disclosure.

The PCR amplification products were screened for positive clones by agarose gel electrophoresis, and the results are shown in FIG. 3. Clones 3, 5, 7, and 9 were selected as positive clones and plasmid DNA was extracted from these clones for further verification using the EcoRI and XhoI double enzyme digestion method, as shown in FIG. 4. As expected, the double enzyme produced a 720 bp DNA fragment. The positive clones were then sent to Suzhou Genewiz Biotechnology Co., Ltd. for sequencing validation.

5. Preparation of high-purity endotoxin-free plasmids: The high-purity endotoxin-free plasmids were prepared according to the instructions provided in the OMEGA Endotoxin-Free Plasmid Prep Kit (purchased from OMEGA Corp.). The specific steps are as follows.

1) Adding 4 mL of LB medium and 4 μL of the corresponding antibiotic to a 15 mL tube; picking a single colony from the plate and add it to the tube; incubating at 37° C. with shaking at 200 rpm for 5.5 hours.
2) Transferring the bacterial culture into a 1 L flask containing 30 mL of LB medium and adding 35 μL of ampicillin (1:100); incubating at 37° C. with shaking at 200 rpm overnight.
3) Pouring the bacterial fluid into a 50 mL centrifuge tube and centrifuge it at 3,500 rpm for 15 minutes to collect the bacterial pellet at the bottom of the tube.
4) Completely resuspend the bacterial pellet with 1 mL of Solution 1/RNaseA (stored in a 4° C. refrigerator) by repeated pipetting; shaking the mixture on a shaker for 30-60 seconds, and then evenly distributing the bacterial suspension into two 2 mL centrifuge tubes (i.e., 500 μL per tube).
5) Adding 500 μL of Solution II to each tube (if Solution II has precipitated, it should be heated), and gently invert the tubes 10-15 times; incubating at room temperature for 3 minutes.
6) Adding 250 μL of N3 to each tube and mixing by inverting the tubes up and down 10 times; incubating for 3 minutes; centrifuging the tubes at 13,000 rpm for 15 minutes; transferring the supernatant to a new centrifuge tube (and discarding the precipitate), and measuring the volume of the supernatant.
7) Adding 0.1 volume of ETR solution (stored in the 4° C. refrigerator) to the supernatant and mixing thoroughly by inverting the tube (if the transferred supernatant is 1,200 μL, adding 120 μL of ETR solution) (Note: ETR solution likely refers to Triton X-114).
8) Placing the centrifuge tube in ice and let it stand for 10 minutes; taking out the tube every 2-3 minutes and invert it several times. (After adding ETR solution, the lysate will become turbid; and it will become clear after being placed on ice).
9) After a 10-minute ice bath, placing the lysate in a 42° C. water bath for 5 minutes, and the lysate will become turbid again. (Note: adjusting the water bath temperature to 70° C. for a warm bath).

10) Centrifuging the solution at 13,000 rpm for 8 minutes at 25° C.; precipitating the ETR solution at the bottom of the centrifuge tube (the precipitate is polysaccharide and endotoxin); transferring the supernatant to a new 2 mL centrifuge tube; adding 0.5 times the volume of anhydrous ethanol; inverting the tube 10 times and let it stand at room temperature for 2 minutes.

11) Inserting two pre-equilibrated HiBind DNA collection columns II into 2 mL collection tubes; adding 700 μL of bacterial lysate supernatant and centrifuging at 13,000 rpm for 1 minute; discarding the flow-through liquid.

12) Adding the remaining bacterial lysate to the HiBind DNA collection columns II; centrifuging at 13,000 rpm for 1 minute, and discarding the flow-through liquid; repeating these steps until all bacterial lysates have been filtered.

13) Adding 500 μL of HBC buffer (isopropanol must be added to new HBC buffer before use) to the HiBind DNA collection columns II; centrifuging at 13,000 rpm for 1 minute and discarding the flow-through liquid.

14) Adding 700 μL of DNA wash buffer (100% ethanol must be added to new DNA wash buffer before use) to the HiBind DNA collection columns II; centrifuging at 13,000 rpm for 1 minute and discarding the flow-through liquid.

15) Washing the HiBind DNA collection columns again with 700 μL of DNA wash buffer; after discarding the flow-through liquid, centrifuging at 13,000 rpm for 2 minutes to ensure complete removal of residual ethanol in the DNA collection columns.

16) Placing the DNA collection columns in new sterile 1.5 mL centrifuge tubes (cut off the cap for centrifugation), and letting them rest at room temperature for 5 minutes to allow complete evaporation of ethanol; adding 120 μL of preheated (70° C.) elution buffer to the center of the membrane and let it rest at room temperature for 1 minute.

17) Centrifuging at 13,000 rpm for 1 minute; combining the eluted DNA from the two tubes into a new sterile 1.5 mL centrifuge tube in a clean bench, then measuring the DNA concentration and storing the DNA at −80° C.

Embodiment Two: Preparation of Inducible CSF1R.CAR Modified T Lymphocytes

1. Packaging of Inducible CSF1R.CAR Lentivirus 1.1 Seeding of 293T Cells

Preparing a single-cell suspension of healthy 293T cells by digesting them with 0.25% trypsin and adjusting the concentration to 4×105/ml; seeding 10 ml of the single-cell suspension in a 10 cm culture dish and incubating overnight at 37° C. with 5% $CO_2$ in a cell culture incubator; the next day, the cells should reach 80% confluence.

1.2 Transfection of Plasmids

Adding 3 μg of pMD2G, 6 μg of psPAX2, and 7.5 μg of the CAR lentiviral vector plasmid to 150 μl of OPTI-MEM medium and mixing them evenly; taking 25 μl of Lipo2000 and adding and mixing it to 500 μl of OPTI-MEM medium; letting it rest at room temperature for 5 minutes; adding the plasmid mixture to the Lipo2000 slowly, mixing them and let the mixture rest at room temperature for 15 minutes; adding the mixture dropwise to the culture dish and mixing it evenly; after 6 hours, replacing with fresh DMEM medium containing 10% FBS.

1.3 Collecting the Supernatant and Concentrating the Virus

After 48 hours of cell culture, the medium containing lentivirus was collected and centrifuged at 1,500 g, 4° C. for 10 minutes to remove cellular debris. The virus-containing supernatant was then filtered through a 0.45 μm membrane. The filtrate was mixed with 5xpEGit virus concentration solution at a ratio of 4:1. The mixture was left to rest overnight at 4° C. and then centrifuged at 3,200 rpm, 4° C. for 10 minutes. The supernatant was discarded, and the virus pellet was resuspended in DMEM medium containing 5% FBS. The virus was aliquoted into 200 μL/tube and stored at −80° C. The purified virus titer was determined using a qPCR titration assay kit (purchased from Zhenjiang ABM Biotechnology Co., Ltd.), and the virus titer was determined to be $1\times10^8$ PFU/mL.

2. Isolation and Activation of PBMCs 2.1 Isolation of PBMCs

To obtain PBMC cells, 10 mL of peripheral venous blood from a healthy plasma donor was collected in an anticoagulant tube. The blood was diluted with an equal volume of PBS and subjected to density gradient centrifugation using lymphocyte separation medium to obtain PBMC cells.

Once PBMC cells were successfully isolated, they were cultured in T551 medium containing 10% FBS at 37° C. with 5% CO 2 in a cell culture incubator.

2.2 Activation of PBMCs

Using T cell culture medium containing 1 μL/mL IL-2 to prepare a suspension of PBMC cells at a concentration of $1\times10^6$/mL. Seeding the cells onto a 24-well cell culture plate coated with CD3/CD28 antibodies to obtain activated T cells. The specific activation parameters are shown in Table 1.

TABLE 1

| Activation Conditions | | |
|---|---|---|
| PBMC cells | Volume of Culture Medium | Time of Activation |
| $1.5\times10^6$/well | 1.5 mL/well | 48 h |

3. CAR-T Cell Preparation

Using the lentivirus prepared in step 1 to transduce the T cells activated in step 2 with an MOI of 20, to produce T lymphocytes modified with CSF1R.CAR.

4. Induction of CSF1R Expression Using DOX

The CAR-T cells prepared in step 3 was cultured in a 24-well plate and induced to express CSF1R.CAR molecule by adding 1 μg/ml of DOX.

5. Detecting the Expression of CSF1R.CAR Molecule by Flow Cytometry

Figure 5:
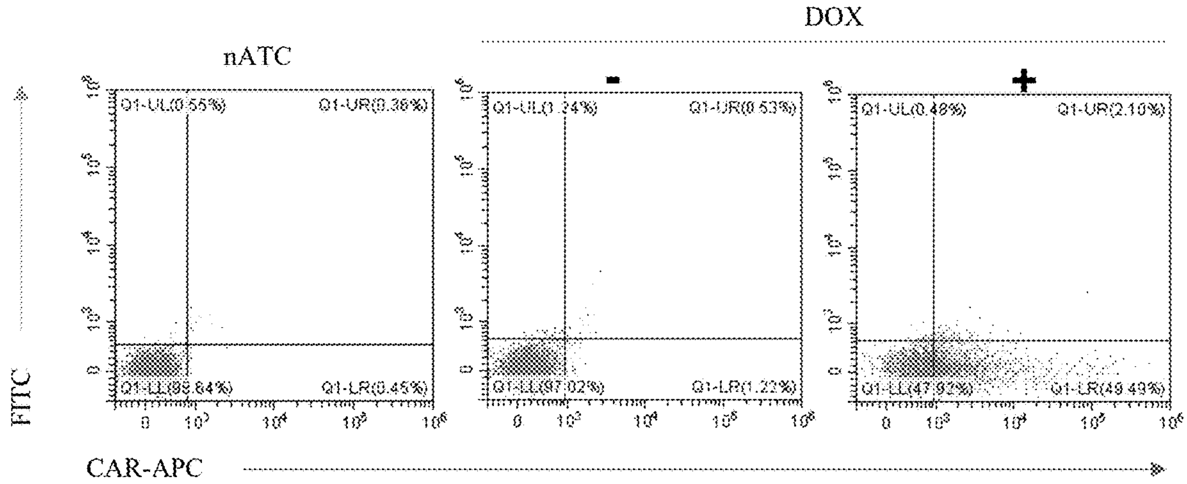
FIG. 5 shows the expression of CSF1R CAR lentivirus transduction in T cells detected by flow cytometry after inducing with DOX for 48 hours.
Figure 6:
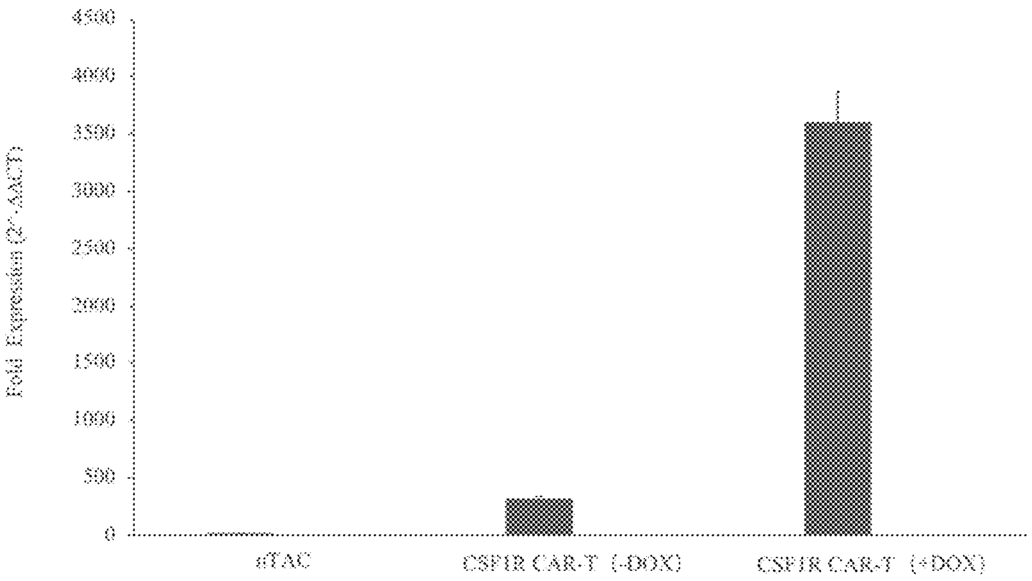
FIG. 6 depicts the results of qPCR analysis used to detect the mRNA expression levels of CSF1R CAR in T cells induced with DOX for 48 hours.

Using a flow cytometry with detection antibody that recognizes the Fab region of the CAR, the expression efficiency of CSF1R.CAR in the prepared CAR-T cells was determined. Specifically, 2×10 5 induced CAR-T cells were stained with anti-mFAB-APC antibody for 30 minutes, followed by flow cytometry analysis to determine the positivity rate of CAR expression. The results are shown in FIG. 5.

It is apparent that the expression time and level of the chimeric antigen receptor in this disclosure are regulated by the induction agent DOX added at specific time and dose. The CAR-T cells showed an increased expression rate after DOX induction.

Figure 7:
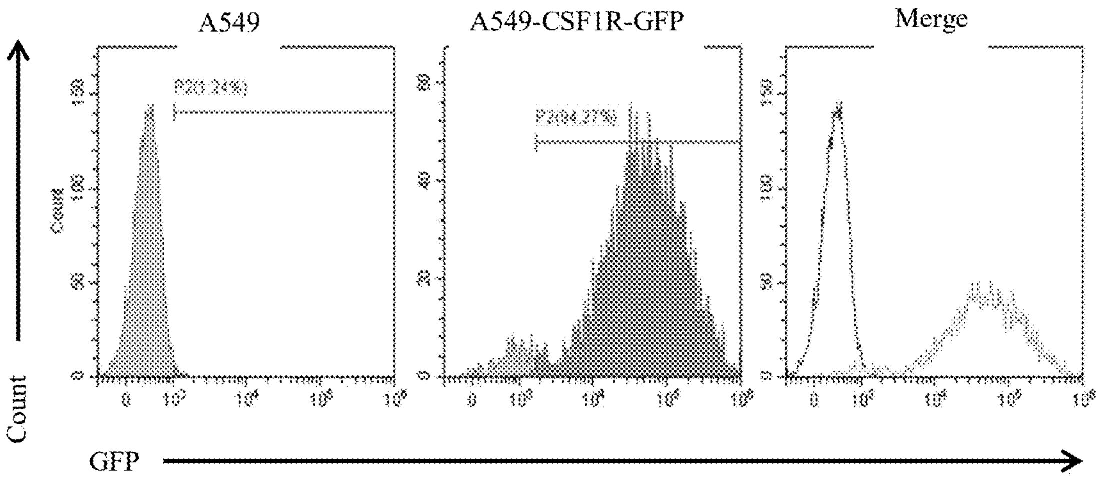
FIG. 7 illustrates the flow cytometry analysis of CSF1R expression in A549-CSF1R-GFP stable transfectants.

Embodiment Three: Detection of the Killing Effect of CSF1R.CAR-T Cells on Target Cells Overexpressing CSF1R 1. MTS Assay for Measuring Cytotoxicity After co-culturing target cells and induced CAR-T cells at different E:T ratios in a 96-well plate, the CSF1R overexpressing target cells were collected and analyzed for their CSF1R expression efficiency using flow cytometry. As shown in FIG. 7, it was found that the CSF1R positive rate of A549 cells was as high as 94%.

Figure 8:
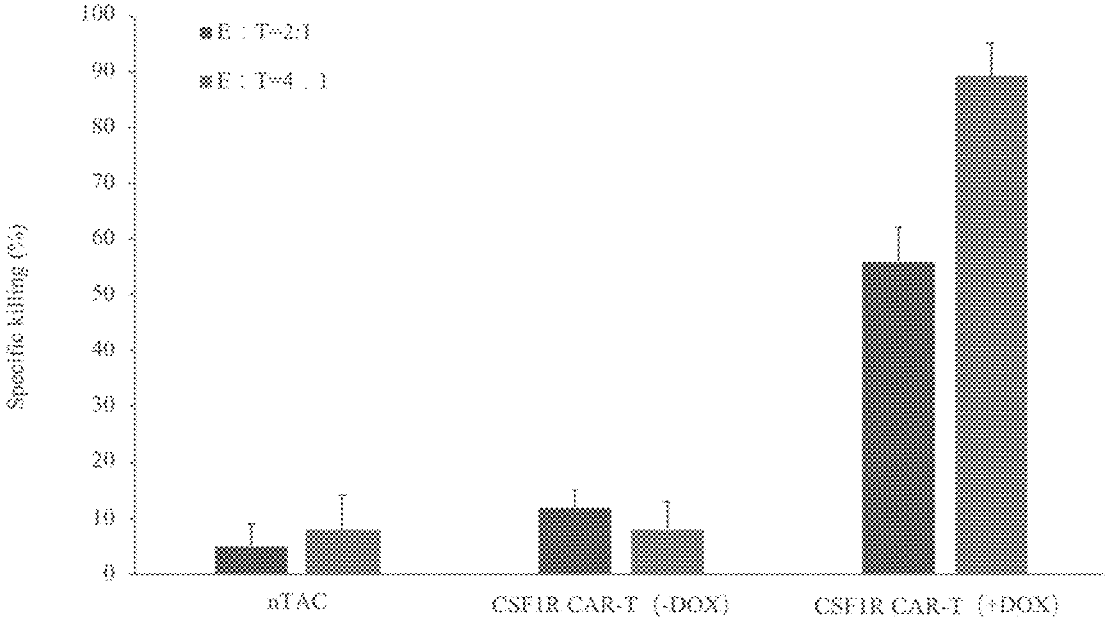
FIG. 8 depicts the MTS assay conducted to evaluate the cytotoxic effects of CSF1R CAR-T cells against A549-CSF1R target cells with and without DOX induction.

After co-culturing T cells and A549-CSF1R-GFP target cells for 24 hours, the MTS assay was used to determine the killing effect of T cells on the remaining tumor cells. As shown in FIG. 8, the results indicate that the present disclosure can induce CAR-T cells to have a significant killing effect on target cells after DOX induction, while untransduced activated T cells and control CAR-T cells without DOX induction showed no significant killing effect.

2. ELISA Method for Detecting the Expression of Cytokines

To verify the activation status of CSF1R.CAR-T cells after killing target cells, T cells were co-cultured with target cells and supernatants were collected at 24 and 48 hours. The levels of IL-2 and IFN-γ in the supernatants were detected using ELISA. The steps of the ELISA experiment were conducted according to the instructions of the ELISA kit (purchased from BD Company, USA).

The specific operations steps are as follows.

(1) Antibody coating: Diluting the coating antibody according to the instructions of the kit and adding 100 μL per well to the ELISA 96-well plate; incubating overnight at 4° C. in a refrigerator.

(2) Collecting supernatants: Collecting the culture supernatants from the co-culture killing experiment and diluting them accordingly.

(3) Blocking: Discarding the coating solution and washing the plate with wash buffer for 3 times; adding 200 μL of 1× Assay Buffer to each well, and incubating at room temperature for 1 hour to block the coated wells.

(4) Additional of sample and standard: Discarding the blocking buffer, washing the wells 3 times with wash buffer, and adding 100 μL of standard or sample with varying concentrations to each well, and incubating at room temperature for 2 hours.

(5) Washing: Discarding the sample solution and the standard solution, washing the wells 5 times with wash buffer.

(6) Additional of detection antibody and horseradish peroxidase: Adding 100 μL of the diluted detection antibody and horseradish peroxidase mixture to each well, followed by incubation at room temperature for 1 hour; then washing the wells 7 times with wash buffer.

(7) Color development: Adding 100 μL of TMB substrate solution to each well and incubating at 37° C. in the dark for 5-30 minutes; then, adding 50 μL of stop solution to terminate the reaction; absorbance readings at a wavelength of 450 nm using an ELISA reader within 30 minutes.

Figure 9:
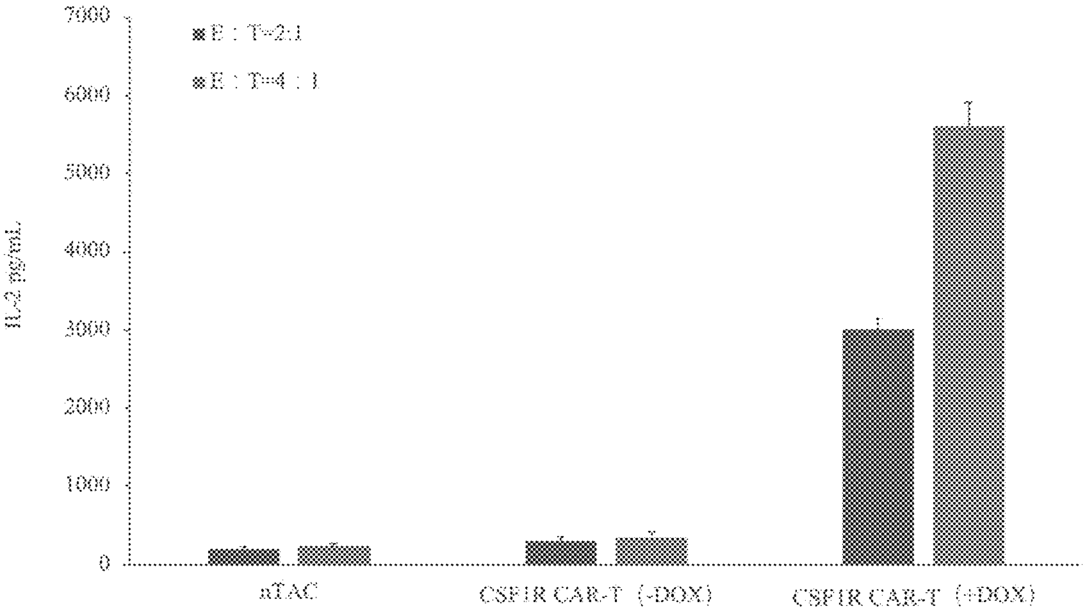
FIG. 9 illustrates the IL-2 expression after target cell killing by the inducible CSF1R.CAR-T cells according to the present disclosure.
Figure 10:
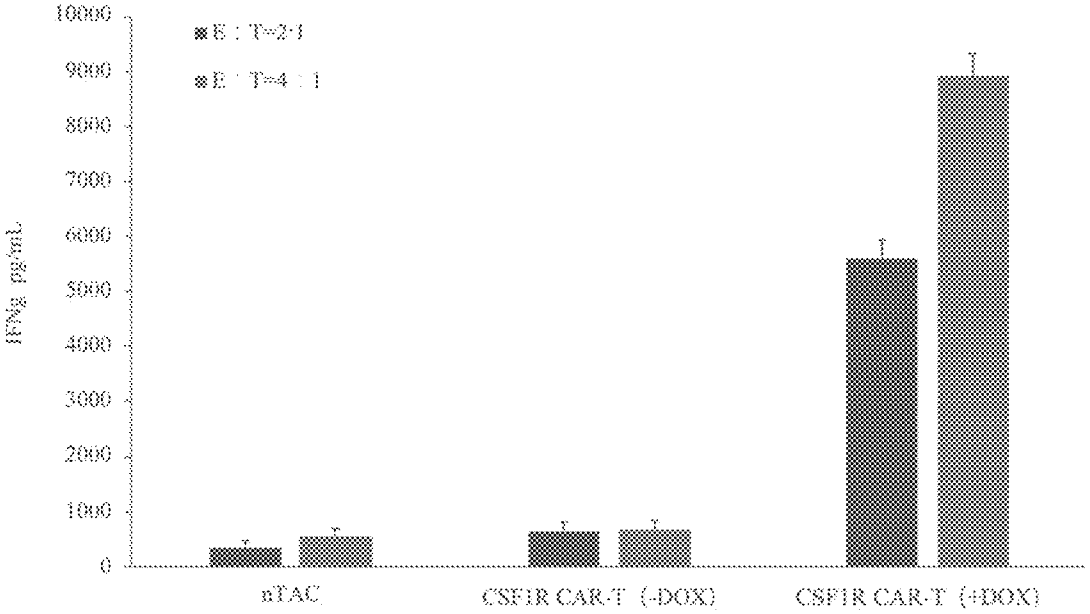
FIG. 10 illustrates the IFN-γ expression after target cell killing by the inducible CSF1R.CAR-T cells according to the present disclosure.

(8) Constructing a standard curve based on the OD450 value of the standard, and calculating the concentration of cellular factors in the sample to obtain the results shown in FIG. 9 and FIG. 10.

From the above embodiments, it can be seen that the expression time and level of the chimeric antigen receptor in the present disclosure are regulated by the addition time and dosage of the induction agent DOX. In the presence of DOX, CAR-T cells specifically kill CSF1R-positive target cells and secrete cytokines IL-2 and IFN-γ. After removing the inducer DOX, CAR-T cells rarely have cytotoxic effect on CSF1R-positive cells and no longer secrete cytokines IL-2 and IFN-γ. The use of CAR-T cells in the present disclosure can regulate the targeted killing of cells and control the level of cytokine secretion, effectively avoiding the potential "cytokine storm" side effects that may occur when CAR-T cells are used for therapy.

The above description is merely embodiments of the present disclosure and does not limit the scope of the patent. Any equivalent structural or procedural modifications made using this disclosure and its accompanying drawings, or direct or indirect application to other relevant arts, are also included within the scope of the present disclosure.

What is claimed is:

1. A chimeric antigen receptor, comprising:

a single-chain variable fragment (scFv) antibody against human CSF1R;

a truncated hIgG1 hinge region SH;

a T cell co-stimulatory signaling molecule; and a T cell intracellular signaling domain, wherein transcription of the chimeric antigen receptor is regulated by an inducible expression element, wherein the inducible expression element is a tet operator; and wherein the chimeric antigen receptor is encoded by the nucleotide sequence of SEQ ID NO: 1.

2. The chimeric antigen receptor according to claim 1, wherein the nucleotide sequence of the tet operator is shown as SEQ ID NO:5.

3. The chimeric antigen receptor according to claim 1, wherein the amino acid sequence of the truncated hIgG1 hinge region SH is shown as SEQ ID NO: 4.

4. The chimeric antigen receptor according to claim 1, wherein the T cell co-stimulatory signaling molecule comprises one or more of CD28, 41BB, and OX40.

5. The chimeric antigen receptor according to claim 1, wherein the T cell intracellular signaling domain comprises a CD3 zeta intracellular signaling activation domain.

6. The chimeric antigen receptor according to claim 1, wherein the chimeric antigen receptor comprises an N-terminal signal peptide having the amino acid sequence as shown in SEQ ID NO:3.

7. The chimeric antigen receptor according to claim 1, wherein the amino acid sequence of said chimeric antigen receptor is shown as SEQ ID NO:2.

8. A recombinant lentivirus, comprising the chimeric antigen receptor according to claim 1.

9. A CAR-T cell, comprising the chimeric antigen receptor according to claim 1, or the recombinant lentivirus according to claim 8.

10. A method for treating Alzheimer's disease in a subject in need thereof, comprising administering to the subject a therapeutically effective amount of the CAR-T cell according to claim 9.

* * * * *